United States Patent [19]

Leu

[11] Patent Number: 5,061,815

[45] Date of Patent: Oct. 29, 1991

[54] METAL LYSINE COMPLEXES AND METHOD FOR PRODUCING METAL LYSINE COMPLEXES

[75] Inventor: Monty Leu, Laurens, Iowa

[73] Assignee: Zinpro Corporation, Edina, Minn.

[21] Appl. No.: 530,200

[22] Filed: May 29, 1990

Related U.S. Application Data

[63] Continuation of Ser. No. 215,573, Jul. 6, 1988, abandoned, which is a continuation-in-part of Ser. No. 98,480, Sep. 18, 1987, abandoned.

[51] Int. Cl.$^5$ ................................................. C07F 3/06
[52] U.S. Cl. .................................... 556/118; 556/134; 426/74; 514/494
[58] Field of Search ................. 556/45, 110, 118, 138, 556/134; 514/502; 426/74

[56] References Cited

U.S. PATENT DOCUMENTS

| | | | |
|---|---|---|---|
| 2,388,372 | 11/1965 | Stewart | 556/134 |
| 2,745,859 | 5/1956 | Norton et al. | 556/134 |
| 3,248,204 | 4/1966 | Knell et al. | 556/134 |
| 3,463,858 | 8/1969 | Anderson | 424/289 |
| 3,742,002 | 6/1973 | Ohlson et al. | 260/439 R |
| 3,899,521 | 8/1975 | Evers | 514/866 |
| 3,941,818 | 3/1976 | Abdel-Monem | 260/429.9 |
| 3,950,372 | 4/1976 | Abdel-Monem | 556/50 |
| 4,021,569 | 5/1977 | Abdel-Monem | 424/289 |
| 4,039,681 | 8/1977 | Abdel-Monem | 556/134 |
| 4,067,994 | 1/1978 | Anderson et al. | 424/295 |
| 4,167,564 | 9/1979 | Jensen | 556/134 |
| 4,172,072 | 10/1979 | Ashmead | 556/134 |
| 4,216,143 | 8/1980 | Ashmead | 556/134 |
| 4,425,280 | 1/1984 | Ho | 556/134 |
| 4,618,625 | 10/1986 | Vinas | 556/134 |
| 4,758,439 | 7/1988 | Godfrey | 426/74 |
| 4,764,633 | 8/1988 | Anderson et al. | 556/50 |
| 4,830,716 | 5/1989 | Ashmead | 204/72 |

FOREIGN PATENT DOCUMENTS 44-20614  9/1969  Japan.

OTHER PUBLICATIONS

Nyberg, Sister M. Helen Therese and Cefola, M., *Arch. Biochem. Biophys.* 111, 327–334 (1965).
Albert, Al, *Biochem. J.* 50, 691–697 (1952).
Perkins, D. J. *Biochem. J.* 55, 649–652 (1953).

*Primary Examiner*—Asok Pal
*Assistant Examiner*—P. Achutamurthy
*Attorney, Agent, or Firm*—Zarley, McKee, Thomte, Voorhees, & Sease

[57] ABSTRACT

A number of metal lysine hydrochloride complexes are produced according to described preparation methods. The complexes are of the formula $$[\text{Lys}]_{m-n}(M)_y X_z$$

wherein: [Lys] is the amino acid lysine; M is a metal ion of either iron, copper, zinc, manganese, or cobalt; m is the valency of the selected metal ion; n is a positive integer less than m; y and z are integers selected to electrostatically balance the cationic and anionic charges of the metal lysine complex; and X is an anion selected from the group including hydroxides, halides, sulfates, phosphates, carbonates, and acetates. The metal lysine hydrochloride complexes are prepared by dissolving in water an oxide or salt of the metal. To the aqueous solution, a quantity of lysine monohydrochloride in a molar ratio to the metal ion of between 0.5 and 4.0 is added and the solution is heated to between 20° C. and 100° C. The metal lysine hydrochloride complexes are used in dietary supplementation, parenteral administration, or topical application of living organisms to raise the intake of the metal by the organism to recommended levels.

3 Claims, No Drawings

METAL LYSINE COMPLEXES AND METHOD FOR PRODUCING METAL LYSINE COMPLEXES

This is a continuation of copending application Ser. No. 215,573 filed on July 6, 1988 abandoned, which is a continuation-in-part application of Ser. No. 098,480, filed Sept. 18, 1987 (now abandoned).

BACKGROUND OF THE INVENTION

The invention relates to metal lysine complexes and, more particularly, to metal lysine complexes, a method of producing the same, and the nutritional supplementation of living organisms with the metal lysine complexes.

It has long been recognized that certain "trace" metals are essential to the health of all living organisms. Such trace metals serve well established functions in enzyme reactions, as components of electrolytes, as binding sites in the transport of oxygen, and as structural components of nonenzymatic macromolecules.

Dietary supplementation is, of course, of greater importance when the organism is being fed a limited diet or ration. For example, agricultural animals are frequently fed a ration comprised of a single grain component, sometimes supplemented by the addition of an amino acid or protein concentrate. Not all of the essential trace metals will be present in biologically required quantities in any single grain, and likely not in any combination ration of two or three grains. With the discovery of the importance of trace metals, dietary supplementation was attempted by the addition of the ionic salts of the trace metals, such as iron sulphate, zinc chloride, copper sulphate, and so on. The bioavailability of the trace metals from the salts is variable because of the poor assimilation of the ionic metal salts in the gastrointestinal track. Dietary supplementation has also been attempted by the use of metal chelates. The binding strength of such compounds to the trace metal component, however, may limit the availability of the metal for assimilation by the organism.

The metal lysine complexes of this invention are formed with iron, copper, zinc, manganese, and cobalt, all of which play important roles in metabolic processes. Iron is the most abundant trace element in the bodies of both humans and animals. The principal function of iron is as the oxygen transport binding site in hemoglobin. Anemia, accordingly, is an early effect of iron deficiency.

Copper plays an important role in several enzymatic functions, particularly the oxidation and transport of iron. Copper has been shown to play a role in the healing process and connective tissue repair, the inhibition of carcinogenesis in laboratory animals, and in the immune function.

Deficiencies of zinc can result in growth retardation, skin lesions, diarrhea, and impaired wound healing. Zinc is necessary for the activity of more than 90 human enzymes associated with carbohydrate and energy metabolism, protein degradation, nucleic acid synthesis, carbon dioxide transport, and many other reactions.

Manganese is associated with a large number of enzymes, such as acetyl-CoA carboxylases and isocitrate dehydrogenase in the Krebs cycle and mitochondria. Manganese is important for the growth and maintenance of connective tissue, cartilage, and bone. While manganese is present in the mineral component of bone, bone manganese is not an available source for use by the soft tissues.

Cobalt is an intrinsic part of vitamin $B_{12}$ and, as such, is required in the synthesis of methionine, an essential amino acid, and in the utilization of odd-numbered carbon fatty acids. While the biological role of cobalt is, as yet, largely unknown, it is known to have an important stimulating effect on the formation of red blood cells.

Lysine is an essential amino acid in the diet of mammals. That is, lysine cannot be synthesized by mammals at a rate adequate to meet metabolic requirements and so must be supplied in the diet. Corn (*Zea mays L.*) is notoriously low in lysine and, if used in a single grain ration, requires lysine supplementation to maintain animal health and for economical animal growth. The present invention, by forming metal lysine complexes, supplements both trace metals and the essential amino acid lysine by the addition of a single dietary supplement. It is believed that the metal component of the metal lysine complex is more easily transported through the intestinal wall with the lysine component than when in the form of an ionic salt. Lesser amounts of the metals, accordingly, may be added to the diet to effect adequate supplementation.

An important object of the invention is to provide an efficient and low cost method for preparing metal lysine complexes which provide readily assimilable forms of the trace metals iron, copper, zinc, manganese, and cobalt and the essential amino acid lysine for the dietary supplementation of these materials in plants, animals, and man.

SUMMARY OF THE INVENTION

The amino acid lysine (Lys) is complexed with a metal ion (M), where M is iron ($Fe^{++}$ or $Fe^{+++}$), copper ($Cu^{++}$), zinc ($Zn^{++}$), manganese ($Mn^{++}$) or cobalt ($CO^{++}$) by reaction in an aqueous solution under acidic conditions of a lysinecontaining compound and a salt of the metal. These complexes are either a 1:1 metal to lysine ([Lys]M) complexsor a 2:1 lysine to metal ([Lys]$_2$M) complex. These complexes, when administered parenterally or as a dietary supplement in animals or as a foliar spray in plants, provide a readily assimiliated source of the metals for use in the metabolic processes of the organism.

DETAILED DESCRIPTION OF THE PREFERRED EMBODIMENT

The metal lysine complexes of the present invention have the formula:

$$[Lys]_{m-n}(M)_y X_z \qquad (1)$$

wherein [Lys] is the amino acid lysine monohydrochloride. In the metal lysine complex formula (1) above, M is a metal ion taken from either iron ($Fe^{++}$ or $Fe^{+++}$), copper ($Cu^{++}$), zinc ($Zn^{++}$), manganese ($Mn^{++}$), or cobalt ($Co^{++}$);

m is the valency of the selected metal ion;

n is an integer less than m;

y and z are integers selected to electrostatically balance the cationic and anionic charges of the metal lysine complex; and X is an anion taken from the group including hydroxides, halides, sulfates, phosphates, and acetates. In the metal lysine complex salts, these anions may be used alone or as a mixture of the anions. In aqueous solution, the anions exist as free ions and the metal lysine complex exists as the cation.

The ionic salts of iron, copper, zinc, manganese, and cobalt are used as sources of the metal ions in the production of the metal lysine complex. Sources of the iron metal ion are ferrous sulfate heptahydrate ($FeSO_4.7H_2O$), ferrous sulfate monohydrate ($FeSO_4.H_2O$), ferrous carbonate ($FeCO_3$), ferrous chloride ($FeCl_2.2H_2O$ and $FeCl_2.4H_2O$), ferric chloride ($FeCl_3$), basic ferric acetate ($FeOH(C_2H_3O_2)_2$), and reduced iron (Fe).

The copper ions can be derived from cupric sulfate pentahydrate ($CuSO_4.5H_2O$), cupric oxide (CuO), cupric acetate monohydrate ($Cu(C_2H_3O_2)_2.H_2O$), cupric carbonate ($CuCO_3$), curprous chloride (CuCl), cupric chloride dihydrate ($CuCl_2.2H_2O$), and cupric sulfate anhydrous ($CuSO_4$).

Sources of the zinc metal ion include zinc oxide (ZnO), zinc sulfate ($ZnSO_4$), and zinc chloride ($ZnCl_2$).

Manganese ion sources are magnanous sulfate tetrahydrate ($MnSO_4.4H_2O$), manganous oxide (MnO), manganous chloride tetrahydrate ($MnCl.4H_2O$), manganese orthophosphate trihydrate ($Mn_3(PO_4)_2.3H_2O$), manganese acetate tetrahydrate ($Mn(C_2H_3O_2)_2.4H_2O$), and manganous carbonate ($MnCO_3$).

Cobalt ion sources include cobalt sulfate heptahydrate ($CoSO_4.7H_2O$), cobalt sulfate monohydrate ($CoSO_4.H_2O$), anhydrous cobaltous chloride ($CoCl_2$), cobalt carbonate ($CoCO_3$), and cobalt acetate ($Co(CH_2.H_3O_2)_2$).

Lysine is a stereoisomer which exists in both the D and L stereoisomer. The L stereoisomer is the biologically active form, and the preferred compound for use in the preparation of metal lysine hydrochloride complex salts because of its commercial availability is L-lysine monohydrochloride. Commercial L-lysine monohydrochloride used in the preferred embodiment is 98.5% pure, such that the lysine activity is 78.8% (80% lysine in L-lysine HCl and 98.5% purity).

The metal lysine hydrochloride complex salts are easily prepared by reacting, under acidic conditions in an aqueous solution, lysine monohydrochloride with one of the previously described metal ion sources. If the metal ion source material to be used is of the oxide, carbonate or metallic form, an inorganic acid is first added to the water prior to adding the metal ion source. The resultant pH of the aqueous solution may be adjusted to be between 1.5 and 4.0. Heating the acidic aqueous solution to near boiling (approximately 80°–85° C.) aids in dissolving some of the metal compounds into solution but is not a necessary part of the process. After the metal ion source compound is in aqueous solution, the lysine source is added in molar ratios of between 0.5 and 4.0 to the amount used of the metal ion source compound. To ensure completeness of the reaction between the metal ion and the lysine hydrochloride, an excess molar ratio of the metal ion source can be utilized. The reaction solution is held at a selected temperature and constantly stirred for approximately 5 to 10 minutes.

After the lysine has been added, the pH of the solution may be raised by the addition of a base or buffering compound, or a mixture of such compounds, such as sodium hydroxide, sodium bicarbonate, sodium sesquicarbonate, and the like. Below a pH of 2.18, the lysine hydrochloride can no longer complex with the metal ion. At pH conditions greater than 2.18, the relative molar quantities of the lysine and metal ion is believed to be the primary determinant of what ratio complexes will be formed. Another factor determining the ratio of lysine to metal in the complexes formed is the pH of the solution; the percentage of higher lysine-to-metal ratio complexes will generally increase with rising pH.

The solution of the metal lysine hydrochloride complexes that results can be administered to organisms, as appropriate, without additional processing. For addition to animal feed rations, however, it is convenient to dry the solution to create a powder or similar dry product. Conventional drying techniques, such as a heated air oven, a vacuum oven, or spray drying, can be used for this purpose.

PREPARATION METHOD 1

One molar equivalent (281.1 grams) of cobaltous sulfate heptahydrate ($CoSO_4. 7H_2O$) and one molar equivalent (185.42 grams) of L-lysine monohydrochloride (98.5% $C_6H_{14}N_2O_2.HCl$) were dissolved in 300 ml of deionized water. The solution was acidified by the addition of hydrochloric acid to a pH of approximately 3.4. The reaction solution was heated, with constant stirring, to a temperature of approximately 80° C. The solution was a dark red in color. A 10 ml aliquot sample was taken and dried in an oven under vacuum. The dried product yielded small crystals of an intense blue. Quantitative chemical analysis of the crystals found 16.74% cobalt, 42.31% lysine hydrochloride, and the remaining 40.95% representing the sulfate and moisture content of the analyzed product, the ratio of cobalt to lysine corresponding to a 1:1 cobalt lysine hydrochloride complex.

PREPARATION METHOD 2

One molar equivalent (249.68 grams) of cupric sulfate pentahydrate ($CuSO_4. 5H_2O$) and one molar equivalent (185.42 grams) of L-lysine monohydrochloride (98.5% $C_6H_{14}N_2O_2.HCl$) were dissolved in 300 ml of deionized water. The solution was heated, with constant stirring, to a temperature of approximately 80° C. The resulting solution was blue in color. A 10 ml aliquot sample was dried in an oven under vacuum, yielding green crystals. Quantitative chemical analysis found the crystals to be 17.27% copper, 5067 lysine hydrochloride, and the remaining 32.06% representing the sulphate and moisture content of the analyzed product. The ratio of copper to lysine corresponding to a 1:1 cupric lysine complex.

PREPARATION METHOD 3

One molar equivalent (79.54 grams) of cupric oxide (CuO) was dissolved in a 300 ml volume of 8.02N aqueous hydrochloric acid heated at 90° C. 185.42 grams (an equimolar quantity) of L-lysine monohydrochloride (98.5% $C_6H_{14}N_2O_2.HCl$) was added and the solution was constantly stirred for three hours. After drying, quantitative analysis showed the presence of a 1:1 copper lysine hydrochloride complex.

PREPARATION METHOD 4

One molar equivalent (278.02 grams) of ferrous sulfate heptahydrate ($FeSO_4.7H_2O$) and one molar equivalent (185.42 grams) of L-lysine monohydrochloride were dissolved in an acidic aqueous solution as in Experiment 1. The pH of the solution was adjusted upwards to 4.5 by use of sodium hydroxide. The resulting solution was dark red in color. Vaccuum oven drying of a 10 ml aliquot sample yielded fine crystals of a dark gold in color. Quantitative chemical analysis showed the crystals to contain 15.78% iron, 49.89% lysine hydrochloride, and the remaining 34.33% representing the sulphate and moisture content of the analyzed product. A ratio of iron to lysine corresponding to a 1:1 iron lysine hydrochloride complex.

PREPARATION METHOD 5

An aqueous solution was prepared by dissolving 159.7 grams zinc sulfate heptahydrate ($ZnSO_4.7H_2O$) in 150 ml of water. An equimolar quantitiy (93.4 grams) of L-lysine monohydrochloride (98.5% $C_6H_{14}N_2O_2.HCl$) was added. The solution was heated with constant stirring to 95° C. A quantity of sunflower hulls (500 grams) was added and the mixture dried in a microwave oven. Seventy-three grams of D,L methionine was added and an additional quantity of sunflower hulls to bring the total weight to two pounds (908 grams).

PREPARATION METHOD 6

One molar equivalent (169.01 grams) of manganese sulfate monohydrate ($MnSO_4.H_2O$) and one molar equivalent (185.42 grams) of L-lysine monohydrochloride were dissolved in water as in Preparation Method 1. Hydrochloric acid was added to reduce the pH of the solution to about 3.4. The solution was heated, with constant stirring, to a temperature of approximately 80° C., and the resulting solution was a dark yellow in color. A 10 ml aliquot sample was dried as in Experiment 1. The dried product was a cream colored flake. Quantitative chemical analysis showed the flakes to be a 1:1 manganese lysine hydrochloride complex.

PLANT EXPERIMENT

A solution containing 0.5% iron was prepared by dissolving 15.85 grams of the iron lysine hydrochloride complex of Experiment 4 in 500 ml of water. This solution was sprayed one time only onto the foliage of iron deficient soybean (*Glycine max* (L.)) plants. Within 24 hours, the yellow color characteristic of iron deficient plants was replaced with the bright green color characteristic of healthy plants.

ANIMAL EXPERIMENTS

In the three Animal Experiments, three complete baby pig rations were formulated, each of which included the following ingredients (per 2000 lbs.) as the base ration:

| Ingredient | Quantity |
| --- | --- |
| Ground Corn | 1250 lbs. |
| Soybean Meal (44% protein) | 350 lbs. |
| Milk Product Supplement[a] | 100 lbs. |
| Animal Fat Supplement[b] | 50 lbs |
| Vitamin and Mineral Supplement[c] | 50 lbs. |
| Medication Supplement[d] | 198 lbs. |
| | 1998 lbs. |

[a]Ingredients: Dried whey, vitamin A acetate; D-activated animal sterol; animal fat preserved with BHA; nonfat dry milk; vitamin E supplement; casein; riboflavin supplement; lecithin; choline chloride; lysine calcium pantothenate.

Guaranteed Analysis:

| | |
| --- | --- |
| Crude Protein, minimum | 20.0% |
| Crude Fat, minimum | 10.0% |
| Crude Fiber, maximum | 0.25% |
| Moisture, maximum | 4.0% |

[b]Ingredients: Animal fat preserved with BHA; dried whey; casein, lecithin

Guaranteed Analysis:

| | |
| --- | --- |
| Crude Protein, minimum | 7.0% |
| Crude Fat, minimum | 60.0% |
| Crude Fiber, maximum | 0.25% |
| Moisture, maximum | 4.0% |

[c]Ingredients: Monocalcium phosphate; dicalcium phosphate; calcium carbonate; yeast culture; fish solubles; soybean meal; dried whey; animal fat stabilized with BHT; L-lysine; vitamin A acetate; D-activated animal sterol; vitamin E supplement; vitamin $B_{12}$ supplement; choline chloride; menadione dimethylpyrimidinol bisulfite; riboflavin supplement; biotin; pyridoxine hydrochloride; calcium pantothenate; niacin; iron sulfate; manganous oxide; copper sulfate; calcium iodate; thiamine hydrochloride; folic acid; ascorbic acid; cobalt carbonate; ethoxyquin; natural and artificial flavors.

Guaranteed Analysis:

| | |
| --- | --- |
| Calcium, maximum | 15.60% |
| Calcium, minimum | 13.00% |
| Phosphorus, minimum | 7.00% |
| Iodine, minimum | 0.005% |
| Vitamin K (menadione) | 72.00 mg/lb. |
| Folic Acid | 20.00 mg/lb. |
| Thiamine | 40.00 mg/lb. |
| Vitamin C | 1.40 g/lb. |

[d]Ingredients: Monocalcium phosphate; dicalcium phosphate; calcium carbonate; salt; yeast culture; fish solubles; fish meal; soybean meal; dried whey; corn distillers dried grains with solubles; casein; animal fat stabilized with BHT; L-lysine; sorbic acid; vitamin A acetate; D-activated animal sterol; vitamin E supplement; vitamin $B_{12}$ supplement; menadione dimethylpyrimidinol bisulfite; choline chloride; riboflavin supplement; biotin; pyridoxine hydrochloride; calcium pantothenate; niacin; sodium selenite; iron sulfate; manganous oxide; copper oxide; copper sulfate; calcium iodate; iron oxide; ethoxyquin; natural and artificial flavors.

Active Drug Ingredients: Carbadox (500 g/ton); pyrantel tartrate (960 g/ton).

Guaranteed Analysis:

| | |
| --- | --- |
| Crude Protein, minimum | 21.00% |
| Crude Fat, minimum | 2.00% |
| Crude Fiber, maximum | 2.00% |
| Calcium, minimum | 8.40% |
| Calcium, maximum | 7.00% |
| Phosphorus, minimum | 3.30% |
| Salt (NaCl), minimum | 3.20% |
| Salt (NaCl), maximum | 2.20% |
| Iodine, minimum | 0.0007% |
| Vitamin $B_{12}$, minimum | 0.67 mg/lb. |
| Vitamin A, minimum | 98,000 USP/lb. |
| Vitamin $D_3$, minimum | 20,200 USP/lb. |
| Vitamin E, minimum | 120 IU/lb. |

Three rations were made up using the above-described base ration as the principal component. The nutrient levels and ingredients used for Rations 1, 2, and 3 were identical except for the source of zinc, lysine, and methionine. So that the Rations 1, 2, and 3 would each contain the same quantities by weight of zinc, lysine, and methionine, two (2) lbs. of a zinc, lysine, and methionine source were included in each 2000 lbs. of the Rations 1, 2, and 3, but different sources of each supplement were used.

| | |
| --- | --- |
| In Ration 1 (2 lbs.) | |
| Zinc from zinc oxide (72% Zn) | 4.0% |
| Lysine from L-lysine hydrochloride (78.5% lysine) | 8.1% |
| Methionine from D,L-methionine (100% methionine) | 8.0% |
| Sunflower Hulls | q.v. |
| In Ration 2 (2 lbs.) | |
| Zinc from ZinPro TM 100 (10% Zn) | 4.0% |
| Lysine from L-lysine hydrochloride (78.5% lysine) | 8.1% |
| Methionine from ZinPro TM 100 (20% methionine) | 8.0% |

| | |
|---|---|
| Sunflower Hulls | q.v. |
| In Ration 3 (2 lbs.) | |
| Zinc from LyZin ™ (10% Zn) | 4.0% |
| Lysine from LyZin ™ (20.25% lysine) | 8.1% |
| Methionine from D,L-methionine (100% methionine) | 8.0% |
| Sunflower Hulls | q.v. |

ANIMAL EXPERIMENT 1

One hundred and twenty head of 30 lb. pigs were divided into three groups of 40 pigs each. The pigs were housed in an open nursery on raised decks with wire floors. Free choice feeders made a wet ration and water feed mixture available to the pigs for consumption on an ad libitum basis. Ration No. 1 was the ration identified above supplemented with zinc oxide, L-lysine monohydrochloride, and D,L methionine. Ration No. 2 was supplemented with ZinPro ®, a commercially available zinc methionine dietary supplement, in an amount as recommended by the manufacturer, ZinPro Corporation. Ration No. 3 was supplemented with LyZin ™, a commercially available zinc lysine hydrochloride product made under the methods of this invention (Preparation Method 5), in the quantity recommended by the manufacturer, LyFe Corporation. Each of the three groups of pigs was fed one of the rations. When one of the groups had first consumed the 1,000 lbs. of its ration, the test was ended. The remaining feed of the other two groups was weighed and all of the pigs in each of the groups were weighed. The results of the test are displayed in the following table.

| Pen/Feed | Ration 1 (Control) | Ration 2 (ZinPro ®) | Ration 3 (LyZin ™) |
|---|---|---|---|
| No. Pigs | 40 | 40 | 40 |
| Starting Weight (lbs.) | 1228 | 1214 | 1211 |
| Avg. Starting Weight | 30.70 | 30.35 | 30.275 |
| Ending Weight | 1723 | 1715 | 1730 |
| Avg. Ending Weight | 43.075 | 42.875 | 43.250 |
| Feed Consumed | 1000 lbs. | 995 lbs. | 982 lbs. |
| Lbs. Gain | 495 | 501 | 519 |
| Avg. Daily Gain (ADG) | 1.125 | 1.138 | 1.179 |
| Feed/Gain | 2.02 | 1.99 | 1.89 |

The group of pigs that had been fed Ration 3, the ration that had been supplemented with the addition of the zinc lysine hydrochloride complex of the present invention, showed an improved average daily gain (ADG) of 4.85% over the group fed the control ration and a 3.38% average daily gain improvement over the group fed the Ration 2 supplemented with the zinc methionine product. The group fed Ration 3 also had a feed-to-gain ratio improvement of 6.44% over the control group and 5.29% over the group fed Ration 2. With feed costs estimated to be 15 cents per pound, the selling price of feeder pigs estimated at $1.00 per pound, and the cost of both ZinPro ® and LyZin ™ fixed at $1.20 per pound, the group fed Ration 3 returned $25.50 more than the control group and $20.05 more than the zinc methionine group.

ANIMAL EXPERIMENT 2

Forty-five head of weaned pigs, averaging 15.78 pounds body weight, were weighed and divided into three groups of fifteen pigs per pen.

| Pig Weights | | |
|---|---|---|
| Pen 4 | Pen 5 | Pen 6 |
| Total 233 lbs. Average per pig 15.53 lbs. | Total 226 lbs. Average per pig 15.07 lbs. | Total 242 lbs. Average per pig 16.13 lbs. |

All rations were bagged and numbered 1, 2, or 3. Ration 1 was the control ration, Ration 2 contained ZinPro ® and Ration 3 contained LyZin ™.

| | Ration 1 (Control) | Ration 2 (ZinPro ®) | Ration 3 (LyZin ™) |
|---|---|---|---|
| Start Weight | 233 | 226 | 242 |
| Finish Weight | 469 | 442 | 479 |
| Gain | 236 | 216 | 237 |
| Feed lbs. | 500 | 450 | 500 |
| ADG | 0.715 | 0.655 | 0.718 |
| F/G | 2.12 | 2.08 | 2.11 |

The pigs whose feed was supplemented with the zinc lysine hydrochloride complex of the present invention showed a 10% improved average daily gain over those pigs whose feed was supplemented with a zinc methionine complex and returned $13.50 more than the zinc methionine group.

ANIMAL EXPERIMENT 3

Eighty-four head of four week old, just weaned pigs, averaging 14.79 pounds body weight, were weighed and divided into six groups of fourteen pigs per pen. They were housed in a Lester nursery with a concrete floor. One-third of the floor was comprised of plastic slats over a pit.

All rations were bagged and numbered 1, 2, or 3. Ration 3 was the control ration, Ration 1 contained 2 lbs/ton ZinPro ®, and Ration 2 contained 2 lbs/ton LyZin ™.

| Pig Weights | | |
|---|---|---|
| Pen 1 and 2 | Pen 3 and 4 | Pen 5 and 6 |
| Total 414 lbs. Average per pig 14.79 lbs. | Total 415 lbs. Average per pig 14.82 lbs. | Total 413.5 lbs. Average per pig 14.77 lbs. |

Pigs in pens 3 and 4 on the LyZin ™ ration consumed more feed, gained faster, and had a slightly improved feed efficiency compared both to the control ration and to the ration containing ZinPro ®, as shown in the following table.

| | Pens 1 & 2 Ration 1 (ZinPro ®) | Pens 3 & 4 Ration 2 (LyZin ™) | Pens 5 & 6 Ration 3 (Control) |
|---|---|---|---|
| Start Weight | 414 | 415 | 413 |
| Finish Weight | 798 | 872 | 770 |
| Gain | 384 | 457 | 357 |
| Feed lbs. | 759.50 | 896 | 751 |
| ADG | 0.55 | 0.65 | 0.51 |
| F/G | 1.98 | 1.96 | 2.10 |

The pigs receiving the zinc lysine hydrochloride supplement of the present invention showed an improved average daily gain of 15% over the zinc methionine group and 22% over the control group. The zinc lysine hydrochloride group also returned $52.53 more than the zinc methionine group and $77.05 more than the control group.

The animal experiments show that the zinc lysine hydrochloride complexes of the present invention provide improved average daily gains in pigs over zinc supplements derived from zinc methionine complexes or from the metal oxide zinc oxide.

I claim:

1. A 1:1 zinc lysine complex of the formula:

$$[Lys](Zn)x_z$$

wherein (Lys) is the amino acid lysine, z is an integer selected to electrostatically balance the cationic and anionic charges of the zinc lysine complex; and x is an anion selected from the group consisting of halide, sulfate, phosphate, carbonate, and acetate.

2. The zinc lysine complexes of claim 1 in crystalline or powdered form.

3. A method of nutritional supplementation of the feed of livestock animals said method comprising adding to the feed ration a small but nutritional supplementing effective amount of a 1:1 zinc lysine complex of the formula:

$$[Lys](Zn)x_z$$

wherein (Lys) is the amino acid lysine, z is an integer selected to electrostatically balance the cationic and anionic charges of the zinc lysine complex; and x is an anion selected from the group consisting of halide, sulfate, phosphate, carbonate, and acetate.

* * * * *